(12) United States Patent
Smith

(10) Patent No.: US 10,220,574 B2
(45) Date of Patent: Mar. 5, 2019

(54) METHOD OF ASSEMBLING A HOUSING FOR A SCANNING ASSEMBLY

(71) Applicant: CapeRay Medical (Pty) Ltd, Cape Town (ZA)

(72) Inventor: Raphael V Smith, Cape Town (ZA)

(73) Assignee: CapeRay Medical (Pty) Ltd, Cape Town (ZA)

( * ) Notice: Subject to any disclaimer, the term of this patent is extended or adjusted under 35 U.S.C. 154(b) by 57 days.

(21) Appl. No.: 15/525,695

(22) PCT Filed: Nov. 12, 2015

(86) PCT No.: PCT/IB2015/058745
§ 371 (c)(1),
(2) Date: May 10, 2017

(87) PCT Pub. No.: WO2016/075648
PCT Pub. Date: May 19, 2016

(65) Prior Publication Data
US 2018/0297293 A1   Oct. 18, 2018

Related U.S. Application Data

(60) Provisional application No. 62/078,669, filed on Nov. 12, 2014.

(51) Int. Cl.
*B29C 65/00* (2006.01)
*B32B 37/00* (2006.01)
(Continued)

(52) U.S. Cl.
CPC ............ *B29C 65/66* (2013.01); *A61B 6/4417* (2013.01); *A61B 6/502* (2013.01); *A61B 8/0825* (2013.01);
(Continued)

(58) Field of Classification Search
CPC ..... B29C 65/48; B29C 65/50; B29C 65/5057; B29C 65/542; B29C 65/66; B29C 65/665;
(Continued)

(56) References Cited

U.S. PATENT DOCUMENTS 1,955,728 A * 4/1934 Allen .................... B23P 11/025
29/282
1,980,156 A * 11/1934 Emrick ................. B23P 11/025
29/252
(Continued)

FOREIGN PATENT DOCUMENTS

EP   0095595 A1   12/1983
FR   2947031 A1 * 12/2010 ........... B29C 65/342
(Continued)

OTHER PUBLICATIONS

International Search Report and Written opinion dated Mar. 7, 2016 in corresponding Application No. PCT/IB2015/058745; 9 pgs.

*Primary Examiner* — Philip C Tucker
*Assistant Examiner* — Brian R Slawski
(74) *Attorney, Agent, or Firm* — Maier & Maier, PLLC

(57) ABSTRACT

A composite housing and a method of assembling a composite housing for a scanning assembly. A body of the housing defines an opening of a first perimeter. A polymethylpentene scanning plate is provided which has lip with a marginally larger perimeter than the first perimeter. During assembly of the composite housing, at least a part of scanning plate is thermally contracted to allow it to be positioned within the opening such that the peripheral side surface of the scanning surface faces the edge of the body. When the scanning plate returns to ambient temperature and expands at least a portion of the side surface of the scanning plate engages the edge of the body.

13 Claims, 2 Drawing Sheets

(51) Int. Cl.

| | |
|---|---|
| *B60J 1/00* | (2006.01) |
| *E06B 3/00* | (2006.01) |
| *E06B 5/00* | (2006.01) |
| *E06B 7/00* | (2006.01) |
| *A61F 13/15* | (2006.01) |
| *B32B 38/00* | (2006.01) |
| *C09J 5/00* | (2006.01) |
| *A61B 5/05* | (2006.01) |
| *B29C 65/66* | (2006.01) |
| *A61B 6/00* | (2006.01) |
| *B29C 65/76* | (2006.01) |
| *A61B 8/08* | (2006.01) |
| *A61B 8/00* | (2006.01) |
| *B29C 65/54* | (2006.01) |
| *A61B 6/04* | (2006.01) |

(52) U.S. Cl.
CPC ............ *A61B 8/4416* (2013.01); *B29C 65/54* (2013.01); *B29C 65/76* (2013.01); *B29C 66/0244* (2013.01); *B29C 66/1122* (2013.01); *B29C 66/126* (2013.01); *B29C 66/12441* (2013.01); *B29C 66/12449* (2013.01); *B29C 66/12469* (2013.01); *B29C 66/24244* (2013.01); *B29C 66/347* (2013.01); *B29C 66/5326* (2013.01); *B29C 66/55* (2013.01); *B29C 66/61* (2013.01); *B29C 66/71* (2013.01); *B29C 66/712* (2013.01); *B29C 66/7212* (2013.01); *B29C 66/7352* (2013.01); *B29C 66/7392* (2013.01); *A61B 6/0414* (2013.01); *A61B 8/403* (2013.01)

(58) Field of Classification Search
CPC ... B29C 65/72; B29C 66/024; B29C 66/0244; B29C 66/139; B29C 66/242; B29C 66/2424; B29C 66/24244; B29C 66/303; B29C 66/30325; B29C 66/304; B29C 66/43; B29C 66/472; B29C 66/71; B29C 66/712; B29C 66/7212; A61B 6/0414; A61B 6/0435; A61B 6/502; A61B 6/025; A61B 6/5247; A61B 8/0825; A61B 8/403; A61B 8/406; A61B 8/4416
USPC .... 156/60, 69, 70, 80, 83, 84, 91, 108, 160, 156/163, 196, 221, 282, 293, 303, 304.1, 156/304.5, 305; 29/592.1; 600/425, 427, 600/436
See application file for complete search history.

(56) References Cited

U.S. PATENT DOCUMENTS

| | | | | |
|---|---|---|---|---|
| 2,038,592 | A * | 4/1936 | Morris | B23P 11/025 29/282 |
| 3,621,550 | A * | 11/1971 | Colestock | B23P 11/025 29/447 |
| 3,724,059 | A * | 4/1973 | Celovsky | B21B 28/02 29/426.1 |
| 4,075,268 | A * | 2/1978 | Nolan | B29C 63/42 156/258 |
| 4,209,896 | A * | 7/1980 | Baboian | C23F 13/20 29/447 |
| 4,305,203 | A * | 12/1981 | Bock | B23P 11/025 29/447 |
| 4,314,396 | A * | 2/1982 | Nunlist | B01F 7/001 29/447 |
| 4,315,336 | A * | 2/1982 | Poler | A61F 2/16 156/182 |
| 5,577,507 | A * | 11/1996 | Snyder | A61B 8/4281 600/472 |
| 6,302,987 | B1 * | 10/2001 | Wojnarowski | H02G 5/005 156/151 |
| 6,584,675 | B1 * | 7/2003 | Rajan | H01J 23/165 216/67 |
| 2010/0155387 | A1 * | 6/2010 | Le Gall | B29C 65/48 219/465.1 |
| 2011/0122617 | A1 * | 5/2011 | Frey | B29C 65/567 362/235 |
| 2015/0327823 | A1 * | 11/2015 | Nariyuki | A61B 6/0414 378/208 |

FOREIGN PATENT DOCUMENTS

| | | |
|---|---|---|
| FR | 2947031 A1 | 12/2010 |
| WO | 2011/153555 A2 | 12/2011 |
| WO | 2014097231 A2 | 6/2014 |
| WO | WO-2014119626 A1 * | 8/2014 ........... A61B 6/0414 |

* cited by examiner

US 10,220,574 B2

METHOD OF ASSEMBLING A HOUSING FOR A SCANNING ASSEMBLY

CROSS-REFERENCE(S) TO RELATED APPLICATIONS

This application claims priority from U.S. provisional patent application No. 62/078,669 filed on 12 Nov. 2014, which is incorporated by reference herein.

FIELD OF THE INVENTION

This invention relates to a method of assembling a composite housing for a scanning assembly used during ultrasound imaging. In particular, but not exclusively, the invention relates to a method of assembling a composite housing for use in dual-modality mammography equipment, which includes a body manufactured from a first material and a scanning surface made from polymethylpentene.

BACKGROUND TO THE INVENTION

Dual-modality imaging systems that use a combination of full-field digital mammography and automated breast ultrasound imaging in a single device are known. These devices combine the benefits of both imaging techniques to obtain more effective and accurate diagnosis of carcinoma or other abnormalities in particularly breast tissue.

The applicant's international patent applications number WO2011/153555 entitled "DUAL-MODALITY SCANNING SYSTEM FOR DETECTING BREAST CANCER" and number WO/2014/097231 entitled "DUAL-MODALITY MAMMOGRAPHY", disclose such dual-modality scanning apparatus that incorporates both X-ray and ultrasound technologies.

WO2011/153555 and WO/2014/097231 are incorporated herein, in their entirety, by reference.

As described in more detail in WO2011/153555 and WO/2014/097231, in use, biological tissue to be scanned, typically a breast, is compressed between a first surface, also referred to as a scanning surface or compression plate, and a compression paddle which is mechanically lowered onto the breast. In one embodiment, the scanning surface forms part of a housing within which a dual modality scanning element comprising an X-ray detector and ultrasonic transducer is mounted on a drive below the scanning surface. Such a dual modality scanning element enables simultaneous acquisition of X-ray and ultrasound images of the breast tissue compressed between the scanning surface and the compression paddle. The scanning element moves on the drive in a plane parallel to the scanning surface for imaging of the tissue through the scanning surface and parallel to a plane defined by the transverse movement of the X-ray source. A linear drive means is provided that moves the scanning element along rails.

In one embodiment the housing is hermetically sealed and is filled with a non-conductive fluid with an acoustic impedance resembling that of the tissue, completely immersing the scanning assembly and drive in the fluid. The purpose of the fluid is to provide ultrasonic coupling between the scanning assembly and the tissue in use. A hermetic seal ensures that the fluid is kept at a constant volume during use. Due to the sealed and filled nature of the housing, the housing is substantially less compressible than it would have been had it not been for the presence of the fluid. The incompressibility of the housing allows both the X-ray detector and ultrasound transducer to move and scan very close to the underside of the scanning surface and, accordingly, the breast tissue, which minimises X-ray signal attenuation that may be caused by the fluid and the geometric magnification due to the finite X-ray focal spot.

The hermetically sealed housing must be devoid of water or air, as it will interfere with the acoustic impedance of the fluid. During manufacturing of the scanning assembly, the filled housing is drained and dried to remove all water and air.

The scanning surface of the housing may be made from polymethylpentene, a thermoplastic material better known commercially by its trade name "TPX®". TPX® is a lightweight polyolefin with exceptional acoustical and electrical properties. TPX® has low moisture absorption and excellent chemical resistance. It is often used for applications requiring low distortion of sound waves including sonar covers, speaker cones, and ultrasonic transducer heads.

Previous approaches used to secure a TPX® plate which forms the scanning surface to a body of a housing include the use of a stitched bond or an adhesive bond. In the latter approach, a special adhesive is used to bond the TPX® plate to the housing. After bonding, more ductile epoxy is used to waterproof the bond. However, TPX® has an unusually low surface tension (24 mN/m) and the epoxy does not adhere to it adequately. In fact, TPX® exhibits excellent peel ability and is often used as a release material at the time of curing thermosetting resins or the like. For this reason, the application of epoxy to the TPX® scanning surface is a cumbersome step in the manufacturing of a hermetically sealed housing incorporating a TPX® scanning surface and may not provide an adequate seal.

The body of the housing, which may have an edge of less than 1 mm thick, needs to be made from a suitably stiff material capable of supporting a compression load of approximately 200 N. The housing is therefore preferably, but not exclusively, made from carbon fibre-reinforced polymers (CFRP). Such materials are easily mouldable into the required shape. To manufacture the entire housing from TPX® is not feasible as the material is not stiff enough.

There is accordingly a need for a method of securing TPX® to a body, preferably made of CFRP in a way that provides adequate sealing characteristics.

In the remainder of this specification the term "scanning plate" should be construed to mean a generally planar piece of material used in a housing of a scanning assembly as described above, which forms the scanning surface through which X-ray and ultrasound imaging of tissue supported on the scanning plate is conducted.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a method of assembling a composite housing for a scanning assembly, the method comprising the steps of:
  providing a body defining an opening of a first perimeter;
  providing a polymethylpentene scanning plate having a lip with a marginally larger perimeter than the first perimeter and a peripheral side surface;
  cooling at least a part of the scanning plate to a temperature of less than or equal to approximately −65° C. so that the perimeter of at least the lip contracts sufficiently to allow the lip to pass through the opening, past an inner edge of the opening;

positioning the cooled scanning plate and the body such that the peripheral side surface faces the edge of the body;

allowing the scanning plate to return to ambient temperature and expand whilst so positioned in the body so that at least a portion of the side surface of the scanning plate engages the edge of the body.

A further feature of the invention provides for the side surface of the scanning plate to define a peripheral groove extending about its periphery, the groove having a selected depth and width such that when the body and the scanning plate are in an assembled condition in which the scanning plate is located within the opening at ambient temperature, a pit of the groove and the edge of the opening in the body engage in an interference fit.

A further feature of the invention provides for the depth of the peripheral groove to be selected such that the pit of the peripheral groove defines a perimeter that is marginally larger than the first perimeter of the opening in the body at ambient temperature.

Yet further features of the invention provide for the method to include the step of positioning a gasket in the groove in the scanning plate prior to positioning the scanning plate and the body, wherein the depth of the peripheral groove is selected such that the gasket in the peripheral groove defines a perimeter that is marginally larger than the first perimeter of the opening in the body at ambient temperature.

Still further features of the invention provided for the method to include the step of providing the scanning plate with a shoulder that projects over the edge of the body in the assembled condition and providing the shoulder and the body with complementary engagement formations, preferably for the shoulder of the scanning plate to be provided with one or more locating flanges and the body to be provided with one or more complementary locating recesses, the locating flanges and recesses being configured to form a mechanical fit when the scanning plate and body is in the assembled condition.

Further features of the invention provide for the method to include the steps of machining stock polymethylpentene to a thickness of between 4 and 6 mm to form the scanning plate; calculating machining dimensions of the scanning plate, taking into account the thermal expansion of the scanning plate during the machining step, such that the pit of the peripheral groove in the scanning plate and the edge of the body will form an interference fit at temperatures above or equal to a minimum operating temperature of the composite housing and machining the scanning plate to the calculated machining dimensions.

A further feature of the invention provides for the minimum operating temperature of the composite housing to be approximately 10° C.

Still further features of the invention provide for the method to include the steps of machining the scanning plate to a marginally larger perimeter to that of the opening; machining the peripheral groove to the selected depth; and for the groove to be machined asymmetrically to form a shoulder and for the complementary engagement formations to be machined onto the shoulder of the scanning plate.

Further features of the invention provide for the scanning plate to be cooled to less than or equal to approximately −65° C. utilising a cooling agent, preferably for the scanning plate to be cooled to approximately −80° C. utilising a cooling agent; and for the cooling agent to be dry ice.

Yet a further feature of the invention provides for the shoulder of the scanning plate defining the one or more locating flanges to be heated while a central region of the scanning plate is cooled to less than or equal to approximately −65° C. so as to substantially prevent fracturing of the shoulder or locating flanges during assembly or disassembly of the scanning plate and the body.

Still a further feature provides for the body to be manufactured from carbon fibre-reinforced polymer; for the body to be moulded into shape so as to define the opening; or for the opening defining the scanning surface to be machined into the body; and for the machined edges of the body to be sealed with epoxy.

A further feature of the invention provides for the method to include the step of introducing a sealant into a juncture between the scanning plate and the body after assembly of the scanning plate within the body and return of the scanning plate to ambient temperature, preferably by injecting a fluid sealant into the juncture and allowing it to set or cure.

Further features of the invention provide for method to include the step of filling the housing with a non-conductive fluid with a specific acoustic impedance of about 1.3 MRayl; for the non-conductive fluid to be oil-based, preferably mineral oil; and for the hermetically sealed housing to contain substantially no water or air.

Still further features of the invention provides for the depth of the groove in the scanning plate to be approximately 1 mm; and for the gasket to be approximately 0.5 mm thick.

In accordance with a second aspect of the invention, there is provided a composite housing for a scanning assembly comprising:

a body defining an opening having an inner edge of a first perimeter; and a polymethylpentene scanning plate secured within the opening, the scanning plate defining a peripheral lip with a marginally larger perimeter than the first perimeter and a peripheral side surface that engages a side edge of the opening when the scanning plate is at ambient temperature with the lip extending past the side edge.

A further feature of the invention provides for the scanning plate to define a peripheral groove with a selected depth such that when the body and the scanning plate are in an assembled condition at ambient temperature, there is an interference fit between a pit of the groove and the side edge of the opening so as to provide a hermetic seal between the body and the scanning plate.

Further features of the invention provide for a gasket to be positioned in the groove in the scanning plate, between the pit and the side edge; and for the depth of the groove to be selected based on the thickness of the gasket.

Further features of the invention provide for the groove in the scanning plate to be asymmetrical such that a shoulder opposite the lip of the scanning plate extends over the side edge of the body when in the assembled condition and wherein the shoulder and the body have complementary engagement formations, preferably one or more locating flanges on the shoulder of the scanning plate and complementary locating recesses in the body that are configured to form a mechanical fit in the assembled condition.

Still a further feature of the invention provides for the scanning plate to have of a thickness of between 4 and 6 mm.

Still further features of the invention provides for the selected depth of the groove in the scanning plate to be approximately 1 mm; and for the gasket to be approximately 0.5 mm thick.

Still a further feature provides for the body to be manufactured of carbon fibre-reinforced polymer.

Further features of the invention provide for the housing to contain a non-conductive fluid with a specific acoustic impedance of about 1.3 MRayl; for the non-conductive fluid to be oil-based, preferably mineral oil; and for the hermetically sealed housing to contain substantially no water or air.

An embodiment of the invention will now be described, by way of example only, with reference to the accompanying drawings.

DETAILED DESCRIPTION WITH REFERENCE TO THE DRAWINGS

Figure 1:
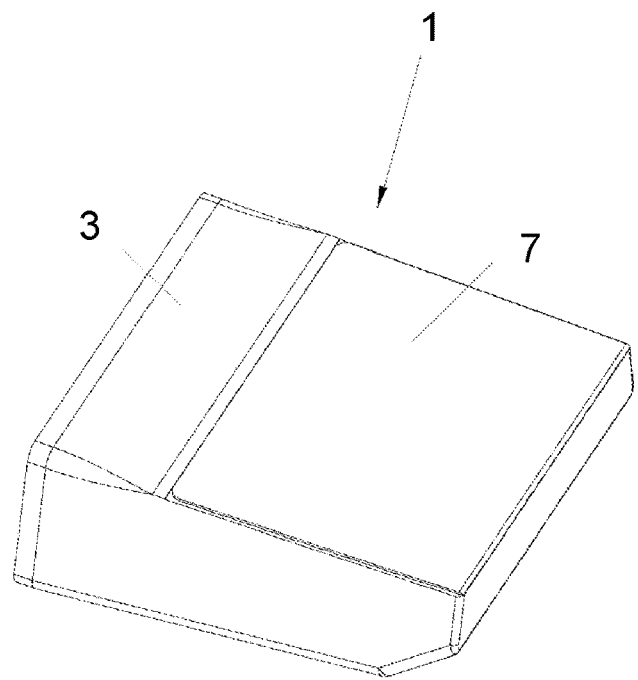
FIG. 1 is a three-dimensional view of a composite housing for a scanning assembly according to the technology in assembled form.
Figure 2:
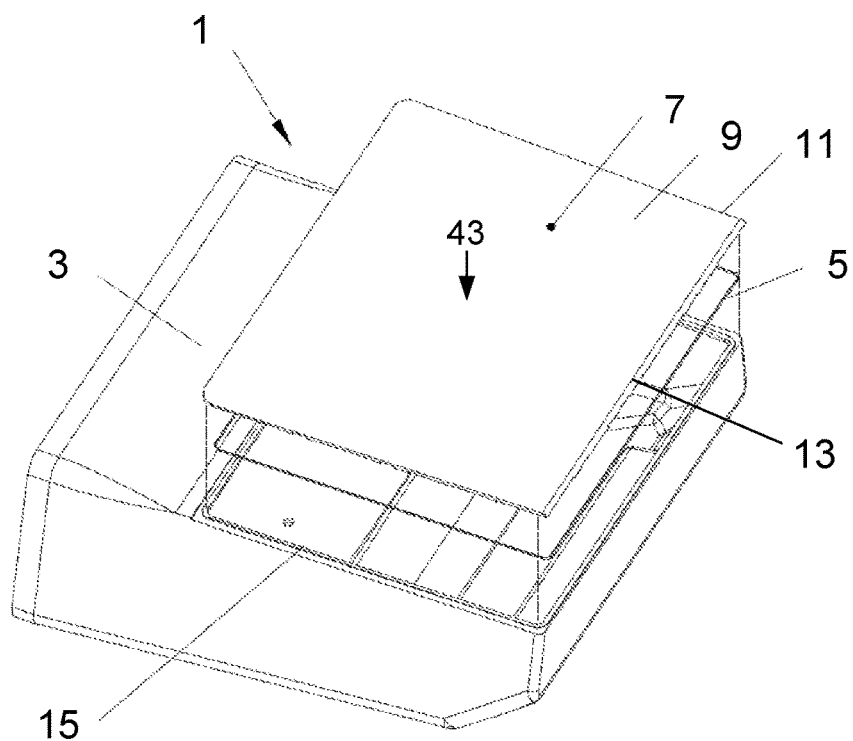
FIG. 2 is a three-dimensional view of the composite housing of FIG. 1 in disassembled form.

A composite housing (1) for a scanning assembly, for use in a dual-modality mammography system according to the technology is shown in FIGS. 1 and 2 in assembled and disassembled forms, respectively. The housing (1) includes a body (3) manufactured from a carbon fibre-reinforced polymer (CFRP), a gasket (5) and a scanning plate (7) manufactured from stock polymethylpentente)(TPX®). In use it should be noted that scanning is conducted by the scanning assembly from within the housing (1), through the scanning plate (7), into biological tissue which is supported on top of the scanning plate (7). For purposes of orientation, the scanning plate (7) defines top (9) and bottom (11) surfaces and a side surface (13) extending about its periphery, it being understood that the top surface (9) is defined on the exterior of the housing (1) and the bottom surface (11) on the interior of the housing (1) when the housing (1) is assembled. In disassembled form, as shown in FIG. 2, the body (3) defines a generally rectangular opening (15) which lies in a scanning plane and into which the scanning plate (7) may be received and secured.

Figure 3:
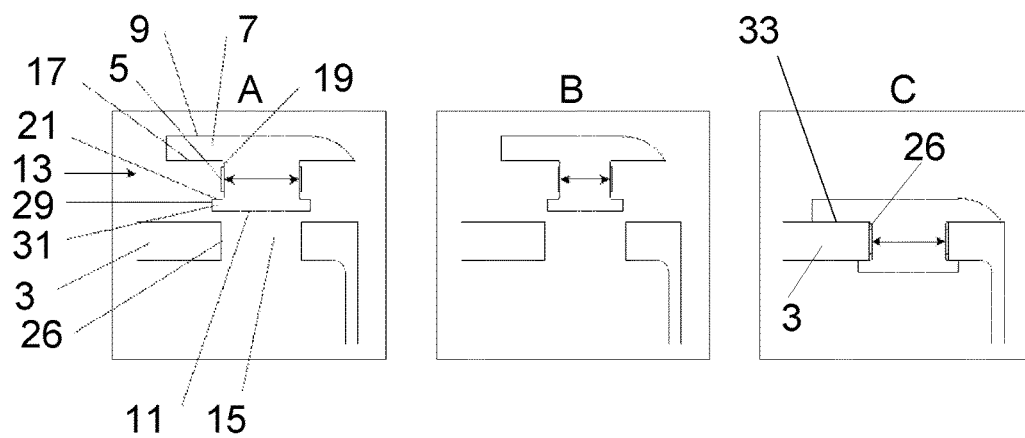
FIG. 3 is a part-sectional representation of a first embodiment of a method of assembling a composite housing for a scanning assembly according to the technology and steps A, B and C broadly outline the method.

Turning now to FIG. 3, a method of assembling the composite housing (1) is outlined in three steps, each step being described here with reference to diagrams A to C shown in FIG. 3, respectively. Diagrams A to C only show part sectional, horizontally condensed side views of the opening (15) in the body (3) and edges of the scanning plate (7) that are to be engaged, but it will be noted that the formations shown generally extend about the entire peripheries of the opening (15) and scanning plate (7). Diagrams A and B show the housing (1) in disassembled, and diagram C in assembled, condition. In the description that follows, while only shown for a single cross-section of the body (3) and scanning plate (7), it will be noted that the features described apply to the entire periphery of both body (3) and scanning plate (7).

As can be seen in diagram A, to facilitate the assembly of the housing (1) and location of the scanning plate (7) in the opening (15) of the body (3), the scanning plate (7) is machined to define locating formations on the side surface (13). An inward step or groove is provided in the side surface (13) as defined by an operatively upper shoulder surface (17), a pit surface (19) and an operatively lower shoulder surface (21). The groove is machined so that, at ambient temperatures, a width thereof, defined by the distance between the upper shoulder surface (17) and the lower shoulder surface (21) corresponds substantially to the thickness of the body (3) at the edge (26) surrounding the opening (15).

In one embodiment of the technology, the stock TPX® forming the scanning plate (7) is machined to a thickness of between 4 and 6 mm and is cut to size to provide a substantially rectangular plate having a marginally larger perimeter than the rectangular opening (15) in the body (3).

The groove is machined in the TPX® so that the shape of the perimeter defined by an outer edge (29) of the lip (31) corresponds substantially to that of the opening (15), and that major dimensions of the bottom surface of the scanning plate (7), measured from opposing outer edges (29) of the lip (31) are, at a minimum operating temperature, which in the current embodiment may be approximately 10° C., approximately 1.6 mm larger than that of the opening (15), in other words approximately 0.8 mm at each end. At ambient temperatures therefore, the scanning plate (7) cannot be inserted into the opening (15) in the body (3). It has been found that these dimension provide a sufficient compression of the gasket seal when the scanning plate returns to ambient temperature.

In addition, the depth of the groove is chosen such that, at a minimum operating temperature, the gasket (5) with a thickness of approximately 0.5 mm is compressed sufficiently between the pit surface (19) of the groove and the edge (26) of the body (3) to provide a hermetic seal. In one embodiment, the depth of the groove is set such that the length of the lower shoulder surface (21) is approximately 1 mm at ambient temperature so as to correspond to the amount of lateral thermal contraction a TPX® scanning plate (7) of approximate length of 230 mm would undergo when it is cooled by means of a cooling agent, preferably dry ice, to approximately –80° C.

Diagram B of FIG. 3 illustrates the manner in which the body (3) and the scanning plate (7) are assembled. To do so, the scanning plate (7) is cooled to a temperature of approximately –80° C. This may be done by, for example, placing the scanning plate (7) in a cooling agent such as dry ice for approximately 15 minutes or more. The scanning plate (7) contracts thermally at the reduced temperature, thereby reducing the major dimensions of the bottom surface of the plate (7), measured from opposing outer edges (29) of the lip (31) by a sufficient amount to enable the lip (31) to pass through the opening (15) in the body (3) without interfering with the edge (26) of the body (3) at the periphery of the opening (15). In the current embodiment, a lateral contraction of approximately 2 mm or more is sufficient to allow the lip (31) to pass through the opening (15). In particular, it will be appreciated that the contraction of the scanning plate reduces the perimeter of the peripheral lip (31) of the scanning plate (7) to such a degree that it is marginally smaller than a perimeter of the opening (15), thereby allowing the lip (31) to pass through the opening (15).

Once the lip (31) has passed through the opening (15) and the groove is aligned with the edge (26) of the opening (15), the scanning plate (7) is allowed to gradually return to its normal operating temperature, resulting in the lateral expansion of the TPX® and associated increase in the major dimensions of the bottom surface (11) of the plate (7) which in turn results in compression of the gasket (5) between the pit surface (19) of the groove and the edge (26) of the opening (15) to form an interference fit that is hermetically sealed as shown in diagram (C).

In the embodiment shown, prior to positioning the cooled scanning plate (7) in the opening, the groove is fitted with a gasket (5) to ensure a hermetic seal between the edge (26) of the opening (15) and the groove (25) in the scanning plate (7) when the scanning plate (7) returns to ambient temperature. In other embodiments the groove may be lined with a sealing material such as rubberised tape in order to achieve a hermetic seal. The thermal expansion of the scanning plate (7) will therefore result in the rubber-lined groove (25) pressing against the edge (26) of the opening (15) in the body (3) to form an interference fit and hermetic seal therebetween. A hermetic seal may also be achieved without a gasket or rubberised tape, provided that the pit surface (19) and the edge (26) of the opening (15) are sufficiently smooth. As discussed before, the hermetic seal is desirable to, in use, prevent the escape of fluid contained in the housing and the ingress of other fluids or air. It should be noted that the scanning plate may be returned to the cooling agent for a further period of time if the fitting of the sealing material or gasket in the groove took longer than a specific period of time, allowing the temperature of the scanning plate to rise above a required temperature.

As is evident from the embodiment of the invention shown in FIG. 3, diagrams A to C, the groove is asymmetrical and when the body (3), gasket (5) and scanning surface (7) have been assembled as shown in diagram (C), the upper shoulder surface (17) projects over an outer surface (33) of the edge (26) of the body (3), so as to support the compression loads on the TPX® scanning plate. The compression load is typically not more than 200 N.

Figure 4:
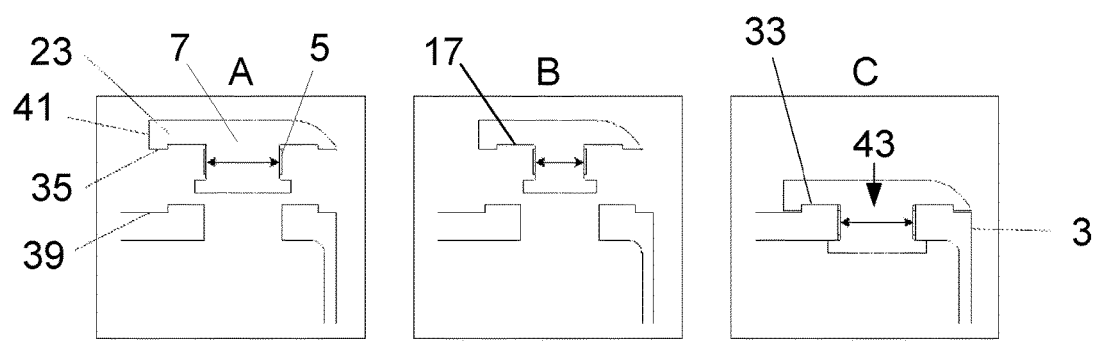
FIG. 4 is a part-sectional representation of a second embodiment of a method of assembling a composite housing for a scanning assembly according to the technology and steps A, B and C broadly outline the method.

Turning now to FIG. 4, a second embodiment is shown in diagrams A to C. In FIG. 4, like reference numerals used with reference to FIG. 3 above are used to refer to like features. As can be seen in FIG. 4, the scanning plate (7) may be machined to include an operatively downwardly projecting locating flange (35) on the operatively upper shoulder surface (17), at or near a radially outer edge (41) of the shoulder (23) formed between the operatively upper shoulder surface (17) and the outer surface (9) of the scanning plate (7). The flange (35) is shaped, dimensioned and positioned to cooperate with a complementary locating recess or slot (39) machined or moulded into the body (3), when the scanning plate (7), gasket (5) and body (3) have been assembled. The flange (35) and slot (39) provide complementary engagement formations that can engage in a mechanical fit to facilitate securing of the scanning plate (7) to the body (3) and prevent relative movement between the scanning plate (7) and the opening (15) once assembled. It is foreseen that, once the body (3) and the scanning plate (7) have been assembled as shown in diagram C of FIG. 4, and a hermetic seal has been obtained between the body (3) and plate (7), that a rubber mallet may be used to apply a force to an operative lateral surface of the housing in order to compress the gasket (5) and engage the flange (35) on the TPX® scanning plate (7) and the slot (39) in the body (3).

When the scanning plate (7) of FIG. 4 is cooled to a sufficiently low temperature, as in the previous example about −80° C., to allow it to contract prior to assembly, the ends or periphery of the scanning plate (7), and more particularly the operatively downwardly projecting locating flange (35) is warmed or heated. In other words, the central region (43), most clearly shown in FIG. 2, of the scanning plate (7) is cooled to less than or equal to approximately −80° C. using dry ice, whilst the peripheral regions of the scanning plate (7) and more particularly the shoulder (23) defining the operatively downwardly projecting locating flange (35) is heated with a heat gun. The locating flange is heated rather than cooled so as to reduce the risk of fracturing of the flanges during assembly or disassembly of the scanning plate and the body. Fracturing is more likely following the exposure of the flanges to −65° C. or temperatures below −65° C. which makes the TPX® material more brittle. It will be appreciated that a suitable cooling and heating system or cryogenic device, capable of cooling the central portion of the scanning plate, whilst heating its periphery can be developed for this purpose. Such a device may use liquid nitrogen as the coolant which, together with air, is directed towards the central portion of the scanning plate and further include a heating coil and blower that releases and directs hot air or steam towards the periphery of the scanning plate.

It will be appreciated that the locating formations on the side surface (13) of the scanning plate (7) of the embodiment of FIG. 3, such as shoulders of the peripheral groove may also be susceptible to fracturing at temperatures below −65° C. and that the periphery of the embodiment of FIG. 3 could also be heated while the central region of the scanning plate is cooled to −65° C. or temperatures below −65° C.

It will be appreciated that the polymethylpentene or TPX® scanning plate may be machined to the required thickness of between 4 and 6 mm out of stock TPX® that may be approximately 10 mm thick. This first machining step releases internal stress in the TPX® which causes it to deform slightly. For this reason, the machining of the scanning plate to the required thickness is done before machining the locating formations into it or providing it with any other critical features. Thereafter, the temperature of the TPX® is measured and the machining dimensions are calculated based on the measured temperature of the TPX®, and taking into account any fluctuation in the temperature of the TPX® scanning plate during the machining process to ensure that the scanning plate is provided with the correct dimensions that will result in compression of the gasket between the TPX® scanning plate and the body at the minimum operating temperature of the composite housing forming part of the scanning assembly, which may for example be approximately 10° C. It is important to note that the dimensions of the TPX® scanning plate will vary with temperature while those of the body may be more constant.

The machining dimensions need to be adjusted at the time of machining based on the temperature of the TPX® at machining time. Specifically the formulas for the lateral and transverse dimensions of the pit of the groove may be represented by:

$$\text{lateral dimension} = 229.6 + 229.6 * 1.17 \times 10\hat{0} - 4 * (\text{temp} - 10° \text{C.})$$

$$\text{transverse dimension} = 297.6 + 279.6 * 1.17 \times 10\hat{0} - 4 * (\text{temp} - 10° \text{C.})$$

Where "temp" is the temperature of the TPX® at the time of machining. This temperature is typically between 15 and 20° C.

In one embodiment, at the time of the thermal fitting the lateral and transverse dimensions of the TPX® must be reduced by about 2 mm to allow the bottom surface of the scanning plate to pass through the opening in the body. To achieve this 2 mm shrinkage, the TPX® must be cooled to at least 75° C. below the minimum operating temperature which is currently 10° C. In other words, in practice it may have to be cooled to about −65° C., although lower temperatures may be acceptable.

As described above, the scanning plate is machined to a shape that corresponds to that of the opening in the body, but is machined to a marginally larger lateral size or perimeter in comparison to the lateral size or perimeter of the opening, such that it is unable to fit through or into the opening at ambient temperatures. Thereafter, the peripheral groove is machined into the edge of the scanning plate to the selected dimensions, which depend, amongst others, on the size of the scanning plate and the temperature to which it will be cooled during use. However, it must be noted that the dimensions of the locating formations on the scanning plate have to be chosen such that the hermetic seal between the scanning plate and body are achieved at the minimum operating temperatures of the scanning assembly. The TPX® scanning plate cannot simply be drastically oversized as this would require cooling the scanning plate to an impractically low temperature during thermal fitting and would result in extensive deformation of the TPX® when it returns to ambient temperature.

The CFRP body is in turn made by means of a moulding process. To do so, a featureless shell is cast between male and female moulds. The opening defining the scanning plane and into which the scanning plate is to be secured, as well as other locating formations, for example the slot referred to above with reference to FIG. 4, are then machined into the shell to form the body. The dimensions of the opening in the body may be selected to accommodate a scanning plate capable of accommodating the largest biological tissue to be measured, typically the largest breast. After the opening has been machined into the body, the open fibres exposed at the machined faces are sealed with a suitable sealant such as an epoxy resin. Alternatively, the CFPR body is moulded into shape so as to define the opening to which the scanning plate is to be secured and so as to define the other locating formations, such as the slot of FIG. 4.

It should be appreciated that the scanning plate must preferably be manufactured from a material which will be able to withstand the compression forces exerted on it by the compressed tissue being imaged. These forces may be as high as 200 N acting over a minimum surface area of 100×100 mm. It has been found that polymethylpentene or TPX® exhibits adequate material strength properties to warrant its use in the scanning assembly. TPX® is a high-performance polyolefin resin with a low density, low dielectric properties, high transparency and low refractive index. Most importantly, it has a lower acoustic impedance (1.84 MRayl) than most other plastic materials with suitable mechanical strength. TPX® provides an acoustic match to both the ultrasonic transducer and the breast tissue, which makes it an ideal material for use as a scanning surface on a platform for dual-modality mammography. As mentioned in the background section of this specification, however, TPX® also has a very low surface tension, providing it with exceptional peel ability. This physical property of TPX® poses a problem associated with fixing the TPX® scanning plate into or onto the body to obtain a hermetic seal. Adhesives meant to provide a hermetic seal, are typically unable to adhere sufficiently to the TPX® plate owing to its low surface tension. Thus there remains a need for a method of assembling a hermetically sealed composite housing comprising a TPX® scanning plate and a body manufactured from a different material, without the use of adhesives.

As described herein, the applicant has developed a solution to this problem by taking advantage of the unusual thermal contraction and expansion properties of TPX®. TPX® has a linear thermal expansion coefficient of about $1.17 \times 10^{-4}$ °C.$^{-1}$, which is significantly larger than the linear thermal expansion coefficients of most common materials. That is to say for every 1 mm of nominal length the scanning plate gets approximately $1.17 > 10^{-4}$ mm larger for every degree of temperature increase. A TPX® scanning plate is therefore able to contract by a substantial amount by cooling it to sufficiently low temperatures. By cooling the scanning plate to a selected temperature, the entire plate contracts and the lateral contraction allows it to fit into the opening provided in the body. As it gradually returns to ambient temperature, the thermal expansion of the plate results in the pit of the groove that is lined with a gasket pressing against the edge of the housing in an interference fit. This method of obtaining a hermetic seal between the body and the scanning plate circumvents the need for the use of adhesives, alleviating the problems associated with applying adhesives to TPX®.

As described before, the hermetically sealed housing may accordingly be filled with a non-conductive fluid with a specific acoustic impedance that resembles the acoustic impedance of the biological tissue to be scanned. In the case of it being breast tissue, an acoustic impedance of about 1.3 MRayl is appropriate. Mineral oil achieves adequate acoustic coupling between the ultrasound transducer, the TPX® scanning plate and the breast tissue. The filling of the housing with oil is conducted during a filling and bleeding process which removes substantially all air from the housing.

The above description is by way of example only and it should be appreciated that numerous changes and modifications may be made to the methods and products described without departing from the scope of the invention. It should, for example, be immediately apparent that the locating flange on the scanning plate and the corresponding slot in the body resemble optional, additional securing features. Likewise, any number of additional or alternative locating and securing formations may be used on the scanning plate and body to achieve substantially the same result. A hermetic seal is still obtained by means of the method described, irrespective of whether the additional engagement features are present. Moreover, the body may be made of any suitable material and not necessarily carbon-fibre reinforced polymer.

It will be appreciated by a person skilled in the art that the shape and size of the opening in the body for the scanning plate and the scanning plate itself may vary according to requirements. Similarly, the depth of the groove and the dimensions of the lip in the scanning plate may also be varied to accommodate gaskets of different thickness.

Alternatively, the groove need not be provided with a gasket and the pit of the groove may abut or interfere directly with the edge of the body. If there are any imperfections in the groove and edge of the body resulting in small cavities between the scanning plate and housing, these cavities can be filled with a sealant. To enhance the hermetic seal between the scanning plate and the edge of the body a sealant may be provided within the peripheral groove after the scanning plate has been assembled within the body and it has returned to ambient temperature. A fluid sealant is injected into the peripheral groove, in other words into the interface between the scanning plate and the body of the composite housing by application of a positive or negative pressure relative to atmospheric pressure which forces the sealant to travel into the peripheral groove, after which the sealant is allowed to set or cure to provide a hermetic seal between the scanning plate and the body. The injection can be carried out using one of two methods:

(i) a negative pressure or vacuum is applied to the housing and a sealant is sparingly applied to the interface between the scanning plate and the body of on the exterior of the composite housing. The negative pressure "sucks" sealant into any cavities in between the scanning plate and the body of the housing; or (ii) sealant is generously applied to the interface between the scanning plate and the body on the inside of the composite housing. A positive pressure is then applied to the housing causing sealant to be "pushed" into any cavities between the scanning plate and the body.

Following injection of the sealant using any one of these methods, the excess sealant is wiped away on the inside and outside of the housing. A urethane-based adhesive, such as Vytaflex®, is used as sealant, however it can be appreciated that any suitably flexible, mineral oil resistant sealant or adhesive can be used as a sealant. A sealant with low viscosity is preferable as it allows the adhesive to travel into smaller cavities. A cyanoacrylate-based adhesive, such as the type of adhesives trading under the tradename "Super Glue", has been found to penetrate well into small cavities due to capillary action.

It will be appreciated that a sealant may also be injected into the peripheral groove provided with a gasket, in order to ensure a hermetic seal between the scanning plate, gasket and the body of the composite housing. The same methods described above may be used to apply the sealant to the interface between the edge of the body and the gasket and the interface between the gasket and the scanning plate.

The depth of the groove and the dimensions of the lip may also be varied to an extent depending, amongst others, on the temperature to which the scanning plate is to be cooled during the assembly process. The sizes and dimensions of the opening, the scanning plate and locating formations will determine the amount of thermal contraction that is required to fit the scanning plate into the body. It therefore follows that the temperature to which the scanning plate must be cooled to facilitate a fit into the opening may vary depending on the amount of contraction of the scanning plate that is required, provided that the properties and integrity of the material remains intact following the cooling step. It should also be apparent that any method of cooling, that may optionally involve any type of cryogen or cryogenic liquid for any appropriate amount of time may be suitable to perform the methods disclosed herein.

It will further be appreciated that the cooling step of the method of assembling a composite housing of a scanning assembly may also be performed in order to disassemble the composite housing, in other words to remove the TPX® scanning plate from the body of the housing.

The method of assembling a composite housing for a scanning assembly may also be employed in the manufacture of ultrasound transducers of different shapes and sizes. For example the body of the ultrasound transducer may be shaped to define a concave or rounded scanning surface. In this embodiment the polymethylpentene plate is rounded, bent or dome-shaped so as to define a round outer surface. The peripheral side surface of the insert and the edges of the body will define the locating formations described herein which allow the insert to be received within the body and hermetically sealed to the body using the methods described herein.

It will similarly be appreciated by one skilled in the art that the housing may be entirely filled with any appropriate fluid of similar properties to mineral oil, depending on the acoustic coupling required. The entire contents of the housing may be immersed within the oil, and the contents of the housing may vary depending on the functions the ultrasound instrument is to perform. The housing may also be provided with suitable connections for connecting the scanning assembly and any other electrical components within the housing to the required circuitry. It will be appreciated by a person skilled in the art that these connections will likewise be hermetically sealed from the surrounding environment by suitable means.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A method of assembling a composite housing for a scanning assembly, the method comprising the steps of:
   providing a body defining an opening of a first perimeter;
   providing a polymethylpentene scanning plate having a lip with a larger perimeter than the first perimeter and a peripheral side surface;
   cooling at least a part of the scanning plate to a temperature of less than or equal to approximately −65° C. so that the perimeter of at least the lip contracts sufficiently to allow the lip to pass through the opening, past an inner edge of the opening;
   positioning the cooled scanning plate and the body such that the peripheral side surface faces the edge of the body;
   allowing the scanning plate to return to ambient temperature and expand whilst so positioned so that at least a portion of the side surface of the scanning plate engages the edge of the body and the lip overlaps the edge of the body.

2. A method as claimed in claim 1, wherein the side surface of the scanning plate defines a peripheral groove extending about a periphery of the side surface, the groove having a selected depth and width such that when the body and the scanning plate are in an assembled condition in which the scanning plate is located within the opening at ambient temperature, a pit of the groove and the edge of the opening in the body engage in an interference fit and wherein the depth of the peripheral groove is selected such that the pit of the groove defines a perimeter that is marginally larger than the first perimeter of the opening in the body at ambient temperature.

3. The method as claimed in claim 2, including positioning a gasket in the groove in the scanning plate prior to positioning the scanning plate and the body.

4. The method as claimed in claim 2, including machining stock polymethylpentene to a thickness of between 4 and 6 mm to form the scanning plate.

5. The method as claimed in claim 4, including calculating machining dimensions of the scanning plate, taking into account a thermal expansion of the scanning plate during the machining step, such that the pit of the peripheral groove in the scanning plate and the edge of the body will form an interference fit at temperatures above or equal to a minimum operating temperature of the composite housing and machining the scanning plate to the calculated machining dimensions.

6. The method as claimed in claim 1, including providing the scanning plate with a shoulder that projects over the edge of the body in the assembled condition and providing the shoulder and the body with complementary engagement formations.

7. The method as claimed in claim 6, wherein the shoulder of the scanning plate is provided with one or more locating flanges and the body is provided with one or more complementary locating recesses, the locating flanges and recesses being configured to form a mechanical fit when the scanning plate and body are in the assembled condition.

8. The method as claimed in claim 7, wherein the shoulder of the scanning plate defining the one or more locating flanges is heated while a central region of the scanning plate is cooled to less than or equal to approximately −65° C. so as to substantially prevent fracturing of the shoulder or locating flanges during assembly or disassembly of the scanning plate and the body.

9. The method as claimed in claim 1, wherein the scanning plate is cooled to approximately −80° C. utilising a cooling agent.

10. The method as claimed in claim 9, wherein the cooling agent is dry ice.

11. The method as claimed in claim 1, wherein the body is manufactured from a carbon fibre-reinforced polymer and the body is moulded into shape so as to define the opening.

12. The method as claimed in claim 1, wherein the body is manufactured from carbon fibre-reinforced polymer and the opening defining a scanning surface is machined into the body to produce the edge of the body, and wherein the machined edge is sealed with epoxy.

13. The method as claimed in claim 1, including introducing a sealant into a juncture between the scanning plate and the body after assembly and return of the scanning plate to ambient temperature.

* * * * *